US012760166B2

(12) United States Patent
Eiden et al.

(10) Patent No.: US 12,760,166 B2
(45) Date of Patent: Oct. 13, 2026

(54) PYROLYSIS OF POLYCARBONATE-CONTAINING MATERIAL IN ORDER TO RECOVER RAW MATERIALS

(71) Applicant: Covestro Deutschland AG, Leverkusen (DE)

(72) Inventors: Stefanie Eiden, Cologne (DE); Rainer Bellinghausen, Odenthal (DE); Aurel Wolf, Wülfrath (DE); Erik Sluyts, Brasschaat (BE); Jonas Krause, Langenfeld (DE); Andreas Seidel, Dormagen (DE)

(73) Assignee: Covestro Deutschland AG, Leverkusen (DE)

( * ) Notice: Subject to any disclaimer, the term of this patent is extended or adjusted under 35 U.S.C. 154(b) by 216 days.

(21) Appl. No.: 18/274,059

(22) PCT Filed: Dec. 22, 2021

(86) PCT No.: PCT/EP2021/087331
§ 371 (c)(1),
(2) Date: Jul. 25, 2023

(87) PCT Pub. No.: WO2022/174963
PCT Pub. Date: Aug. 25, 2022

(65) Prior Publication Data

US 2024/0425665 A1 Dec. 26, 2024

(30) Foreign Application Priority Data

Feb. 17, 2021 (EP) .................................... 21157529

(51) Int. Cl.

| | |
|---|---|
| ***C08J 11/12*** | (2006.01) |
| ***B01J 6/00*** | (2006.01) |
| ***C07C 4/22*** | (2006.01) |
| ***C07C 29/48*** | (2006.01) |
| ***C07C 37/84*** | (2006.01) |
| ***C07C 51/43*** | (2006.01) |
| ***C10B 53/07*** | (2006.01) |
| ***C10B 57/14*** | (2006.01) |

(52) U.S. Cl.

CPC ............... *C08J 11/12* (2013.01); *B01J 6/008* (2013.01); *C07C 4/22* (2013.01); *C07C 29/48* (2013.01); *C07C 37/84* (2013.01); *C07C 51/43* (2013.01); *C10B 53/07* (2013.01); *C10B 57/14* (2013.01); *C08J 2325/06* (2013.01); *C08J 2369/00* (2013.01)

(58) Field of Classification Search

CPC .................................. C08J 11/12; C10G 1/10
See application file for complete search history.

(56) References Cited

U.S. PATENT DOCUMENTS 5,216,149 A * 6/1993 Evans ...................... C10G 1/10 252/182.28
5,821,553 A 10/1998 Evans et al.
2014/0228606 A1* 8/2014 Narayanaswamy ..... B01J 29/40 585/241
2021/0277202 A1 9/2021 Wilhelmus et al.

FOREIGN PATENT DOCUMENTS

JP S63-257933 A 10/1988
JP 2002-265798 A 9/2002
JP 2011236337 A 11/2011
WO WO-2011079894 A2 * 7/2011 ............... C10G 3/60
WO WO-2018224482 A1 * 12/2018 ............. C10G 1/002

OTHER PUBLICATIONS

English machine translation of JP 2011-236337 (Year: 2011).*
International Search Report for International Patent Application No. PCT/EP2021/087331, mailed Apr. 4, 2022.
Written Opinion for International Patent Application No. PCT/EP2021/087331, mailed Apr. 4, 2022.
Antonakou E. V. et al: "Pyrolysis and catalytic pyrolysis as a recycling method of waste CDs originating from polycarbonate and HIPS" Bd. 34, Nr. 12, Dec. 1, 2014 (Dec. 1, 2014), pp. 2487-2493, XP055831472, US. (Abstract Attached).
Vouvoudi Evangelia C. et al: "Thermal degradation characteristics and products obtained after pyrolysis of specific polymers found in Waste Electrical and Electronic Equipment"; Frontiers of Environmental Science & Engineering, Higher Educatino Press, Heidelberg, Bd. 11, Nr. 5, Oct. 10, 2017 (Oct. 10, 2017), pp. 1-10, XP036343343. (Abstract Attached).
Achilias D. S. et al: "Chemical recycling of polymers from Waste Electric and Electronic Equipment", Journal of Applied Polymer Science, Bd. 114, Nr. 1, Oct. 5, 2009 (Oct. 5, 2009), pp. 212-221, XP055831552. (Abstract Attached).
Rajarao Ravindra et al: "Characterization of gas evolution and char structural change during pyrolysis of waste CDs" Journal of Analytical and Applied Pyrolysis, Bd. 105, Jan. 1, 2014 (Jan. 1, 2014), pp. 14-22, XP055831557 NL.

* cited by examiner

*Primary Examiner* — Renee Robinson
(74) *Attorney, Agent, or Firm* — K&L Gates LLP

(57) ABSTRACT

A method for pyrolysis of polycarbonate-containing material in order to recover raw materials is provided. The method comprises at least the following steps: (a) introducing material intended for the pyrolysis, at least comprising material that contains a mixture of a polycarbonate-containing compound and a polystyrene-containing compound, into a reactor; (b) decomposing, at a temperature of 300° C. to 700° C., at least the material intended for pyrolysis introduced into the reactor in step (a) and obtaining a product that is present in the gaseous phase as the pyrolysate and of pyrolysis residues that are present in a non-gaseous phase; and (c) cooling the removed pyrolysate to a temperature of less than 300° C. while obtaining a pyrolysis product, selected from pyrolysis condensate, pyrolysis sublimate or a mixture thereof.

19 Claims, No Drawings

PYROLYSIS OF POLYCARBONATE-CONTAINING MATERIAL IN ORDER TO RECOVER RAW MATERIALS

CROSS REFERENCE TO RELATED APPLICATIONS

This application is a U.S. national stage application, filed under 35 U.S.C. § 371, of International Application No. PCT/EP2021/087331, which was filed on Dec. 22, 2021, and which claims priority to European Patent Application No. 21157529.5, which was filed on Feb. 17, 2021. The contents of which are hereby incorporated by reference into this specification.

BACKGROUND

Polycarbonate-containing material—such as polycarbonate blends, for example polycarbonate resin or polycarbonate composite resin—is used as a material for consumer goods. Corresponding polycarbonate resins or polycarbonate composite resins are made by blending the polycarbonate with other polymers, for example by blending polycarbonate with acrylonitrile-butadiene-styrene (ABS). Because these polycarbonate-containing materials have excellent properties such as impact resistance, flowability, toughness, and flame retardancy, they are used in a large number of applications, such as electronic devices and automobiles.

Subsequent to the marketing of the above polycarbonate resins and polycarbonate composite resins as an element of many commercial products, they accumulate at the end of the service life of the commercial products in waste as materials of value. Old commercial products are mostly sent for disposal and replaced with new commercial products. The total amount of plastic waste this generates increases every year. About 60% of the total amount of this waste is disposed of through incineration or landfill.

When plastic waste is incinerated, $CO_2$ is emitted into the air, which contributes to global heating. Its low density means that plastic waste in landfills occupies a large volume and can from there also contribute to general pollution in rivers and seas. For this reason it is important to develop efficient recycling methods with which the waste problem can be solved and at the same time which also allows fossil resources to be conserved.

Since the abovementioned polycarbonate (composite) resins account for approximately 8% of the polymer market, the recycling of polycarbonates has not thus far been a focus of developments. For the future, the continuing growth of the plastics market does however mean it is important to develop recycling technologies for all polymer classes in order both to reduce $CO_2$ emissions and to conserve fossil energy sources.

The processes for recycling plastic waste can be roughly divided into three categories:

(1) mechanical recycling: Here, the plastic waste is melted down again as is and can then be reused. This is possible for example with very pure PC waste.

(2) chemical and thermochemical recycling: Here, the plastic waste is depolymerized into monomers or broken down into smaller molecules in order to obtain useful chemical raw materials, and (3) thermal recycling, in which the plastic waste is converted into offgas and heat energy.

The chemical raw materials obtained from thermochemical recycling can be used to synthesize new synthetic resins or other chemical products.

Thermochemical recycling is referred to as pyrolysis. In most cases pyrolysis is employed for packaging waste, affording a pyrolysis oil that is used as a kind of recycled naphtha in known refinery processes with crackers in the form of a drop-in solution. The pyrolysis of polycarbonate in this pyrolysis process is something about which little is known.

The use of catalysts or additives in the pyrolysis process can lower operating temperatures, shorten reaction times, increase degradation efficiency, and restrict product distribution, making the process more efficient.

The use of metal halide salts as catalysts, especially copper chloride and iron chloride catalysts, has made it possible to produce phenolic compounds in greater abundance during the pyrolysis of polycarbonate at 600° C. than is the case without a catalyst (M. Blazsó, J. Anal. Appl. Pyrolysis, 1999, 51, 73-88). In addition, the catalytic pyrolysis of polycarbonate has been optimized through the use of various metal chloride compounds with the aim of reducing carbonization residues (J. Chiu et al., Waste Manage., 2006, 26, 252-259). The influence of the catalyst was determined at 400° C. (1 h), since the uncatalyzed pyrolysis proceeds very slowly at this temperature. The choice of metal chloride had a major effect on the pyrolysis. Whereas NaCl, $CrCl_3$, $CuCl_3$, and $AlCl_3$ did not improve pyrolysis rates, $SnCl_2$ and $ZnCl_2$ broke down the polycarbonate with a loss in weight of over 80%.

The use of metal salts as catalysts was likewise able to improve product distribution in the pyrolysis of polycarbonate. Whereas the liquid product in the polycarbonate pyrolysis without catalyst comprised eleven different products, the mixtures with $ZnCl_2$ or $SnCl_2$ as catalyst comprised only seven major products, including bisphenol A, phenol and diphenyl ether, with smaller amounts of impurities.

For the pyrolysis of polycarbonate-containing material, catalysts consisting of metal oxides and zeolites with different porosities and acid/basicity are also known (E. V. Antonakou et al. Polym. Degrad. Stab., 2014, 110, 482-491. M. N. Siddiqui et al., Thermochim. Acta, 2019, 675, 69-76).

With the aid of basic catalysts such as CaO and MgO it was possible to significantly reduce the temperature in the pyrolysis to 400-450° C., with the concomitant production of liquid fractions having high proportions of phenolic compounds (D. S. Achilias et al., J. Appl. Polym. Sci., 2009, 114, 212-221. E. C. Vouvoudi et al., Front. Environ. Sci. Eng., 2017, 11, 9). From a mixture of polypropylene (PP), acrylonitrile-butadiene-styrene (ABS), high-impact polystyrene (HIPS), and polycarbonate it was possible to demonstrate a slow release of BPA and $CO_2$ from polycarbonate at 440° C.

Under the influence of alkaline earth metal oxides and hydroxides (MgO and $Mg(OH)_2$) the steam pyrolysis of pure polycarbonate was able to achieve better efficiency and a higher BPA yield (78%) at 300° C., whereas heating to 500° C. with the use of MgO produced a high proportion of phenol (84%) (T. Yoshioka et al., Polym. Degrad. Stab., 2009, 94, 1119-1124, T. Yoshioka et al., Ind. Eng. Chem. Res., 2014, 53, 4215-4223).

Document US 2007/0185309 A1 describes a method for the depolymerization of polycarbonates with water in the supercritical or subcritical state. A highly pure dihydroxy component (BPA) that is a constituent of polycarbonate was obtained in high yield by this method. This depolymerization method is environmentally friendly, since it does not involve the use of organic solvents. It shows a high breakdown rate and few by-products.

None of the pyrolysis processes described in the prior art is suitable for industrial or commercial use, since they are mostly intended for use as pyrolyses on a microgram scale for analytical purposes. The pyrolyses presented in the prior art are therefore in each case carried out in pyrolysis devices that are not suitable for industrial or commercial use.

Especially for the pyrolysis of larger amounts of polycarbonate-containing materials that also include other ingredients besides polycarbonate, there is a need for novel processes using suitable reactors with which the influence of the other ingredients on the result of the pyrolysis of polycarbonate can be reduced. Despite the presence of other ingredients, polycarbonate-containing polymer mixtures should selectively afford pyrolysis products having a high content of cleavage products that can be reused for polycarbonate synthesis, especially aromatic hydroxy compounds such as bisphenol A (BPA) or phenol. On energy grounds it is preferable if aromatic compounds having at least two hydroxyl groups, especially those of the general formula (I) below, are to a major extent recovered by the pyrolysis, since these can be directly reused for the production of polycarbonates in a polycondensation reaction without further energy-intensive petrochemical transformation steps.

In addition, said novel pyrolysis process should afford a pyrolysis product in which, in addition to the cleavage products that can be reused in polycarbonate synthesis, cleavage products of the other ingredients, for example styrene from polystyrene-containing materials, are also present in significant amounts and good yield and are suitable for the production of said ingredients in the sense of cyclic recycling.

SUMMARY

The object was therefore to provide, for the commercial execution of a pyrolysis, a process and pyrolysis devices employable in said process for the pyrolysis of a pyrolysis feedstock that includes at least material comprising a mixture of polycarbonate-containing compound and polystyrene-containing compound, the use of which affords, even with relatively large amounts of pyrolysis feedstock, an amount of pyrolysis product that comprises, preferably in an amount of more than 40% by weight based on the total weight of polycarbonate-containing and polystyrene-containing material used, cleavage products that can be reused for the synthesis of polycarbonate-containing and polystyrene-containing material. A further object was to recover, to a major extent, aromatic compounds having at least two hydroxyl groups, especially those of the general formula (I) below, through the pyrolysis of a pyrolysis feedstock comprising polycarbonate-containing compound. A further object was to recover through the pyrolysis, to a major extent, aromatic compounds having at least two hydroxyl groups, especially those of the general formula (I) below, and also styrene.

The present application therefore provides a pyrolysis process, comprising at least the following steps:

(a) introducing of a pyrolysis feedstock that includes at least material comprising a mixture of polycarbonate-containing compound and polystyrene-containing compound into a reactor;

(b) degradation of at least the material of the pyrolysis feedstock introduced in step (a) in the reactor at a temperature of 300° C. to 700° C. to obtain a gas-phase product as pyrolysate and a non-gas-phase pyrolysis residue, wherein (i) during said breakdown, the amount of oxygen gas in the reactor is from 0% to 2.0% by volume based on the total volume of the gases present in the reactor, and (ii) during said breakdown, said pyrolysate is discharged from the reactor, and (iii) said pyrolysis residue is discharged from the reactor;

(c) cooling of the discharged pyrolysate to a temperature of less than 300° C. to obtain pyrolysis product selected from pyrolysate condensate, pyrolysate resublimate or a mixture thereof, (d) optionally working up of the pyrolysis product.

DETAILED DESCRIPTION

The term "pyrolysis feedstock" refers to the totality of the substances introduced into the reactor for the pyrolysis that therein undergo thermal treatment in the absence of oxygen gas or in the presence of a reduced amount of oxygen gas. The pyrolysis feedstock is preferably in solid form prior to its introduction into the reactor.

"Pyrolysate" is understood as meaning the totality of the products formed by pyrolysis that are in the gas phase in the reactor under the conditions of step (b) (more particularly in the form of a gas and/or as an aerosol).

"Pyrolysis residue" is understood as meaning the totality of the substances formed by pyrolysis and other residues of the pyrolysis feedstock that are not in the gas phase in the reactor under the conditions of step (b). Preference is given to the embodiments of the process characterized in that the pyrolysis residue in the reactor is solid.

"Pyrolysis product" is understood as meaning the totality of the products from the pyrolysate that in step (c) accumulate by condensation and/or resublimation when the pyrolysate cools. Pyrolysis product that is liquid is also referred to as pyrolysis oil.

Unless explicitly otherwise defined in this connection, a substance (for example material, pyrolysis feedstock, pyrolysate, pyrolysis product, pyrolysis residue) is "liquid" if it is in the liquid state at 20° C. and 1013 mbar. Unless explicitly otherwise defined in this connection, a substance (for example material, pyrolysis feedstock, pyrolysate, pyrolysis product, pyrolysis residue) is "solid" if it is in the solid state at 20° C. and 1013 mbar. Unless explicitly otherwise defined in this connection, a substance (for example material, pyrolysis feedstock, pyrolysate, pyrolysis residue) is "gaseous" if it is present as a gas at 20° C. and 1013 mbar.

A substance is "organic" if its chemical structure includes at least one covalent carbon-hydrogen bond.

In this application, the average molar masses specified for polymers or for polymeric ingredients are unless explicitly otherwise stated always weight-average molar masses Mw, which can in principle be determined by gel-permeation chromatography using an RI detector, it being expedient to perform the measurement against a external standard.

A "polycarbonate-containing compound" is a polymeric compound selected from a homopolymer or copolymer obtained by a polyreaction and where at least one repeat unit contains at least one

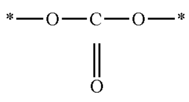

structural unit, where * denotes a valence of the polymer backbone.

In the context of the present application, "polystyrene-containing material" or "polystyrene-containing compound" is understood as meaning a material or a compound, preferably a polymer, containing structural units derived from styrene or styrene derivatives, especially from styrene.

A "polystyrene-containing compound" is in this sense a polymeric compound selected from a homopolymer or copolymer obtained by a polymerization reaction and having as a repeat unit at least one *—$CR^1Ph-CH_2$—* structural unit where * denotes a valence of the polymer backbone, $R^1$ is a hydrogen atom or a methyl group, and Ph is a phenyl group optionally substituted with at least one group selected from $C_1$ to $C_4$ alkyl group and halogen atom (especially chlorine). Said material particularly preferably comprises in addition to at least one polycarbonate-containing compound at least one polymer in the form of a polystyrene-containing compound having at least one structural unit according to the above formula that is derived from styrene ($R^1$=H, Ph=phenyl), α-methylstyrene ($R^1$=methyl, Ph=phenyl), p-methylstyrene ($R^1$=H, Ph=4-methylphenyl), p-chlorostyrene ($R^1$=H, Ph=4-chlorophenyl) or mixtures thereof. Further preference is given to $R^1$=H according to the above formula.

A "reactor" is a volume in which a chemical transformation, for example a thermal breakdown of material from the pyrolysis feedstock, takes place. For a thermal breakdown this can for example be the volume of a heated vessel in which the pyrolysis feedstock is contained.

It is in accordance with the invention advantageous when the pyrolysis feedstock is in accordance with the process of the invention introduced into a reactor characterized in that it is selected from a continuous stirred-tank reactor (CSTR), fixed-bed reactor, fluid-bed reactor, screw reactor, screw-conveyor reactor, entrained-flow reactor, entrainment-flow reactor, rotary-tube reactor, fluid-bed reactor, and drum reactor. More particularly, suitable reactors are preferably ones in which the pyrolysis feedstock can be introduced continuously and are selected in particular from a rotary-tube reactor, continuous stirred-tank reactor (CSTR), fixed-bed reactor (especially with continuous bed exchange (shaft reactor) with internal heat exchangers, preferably with internal heat exchanger tubes), screw reactor, screw-conveyor reactor, entrained-flow reactor, rotary-tube reactor or fluidized-bed reactor. In one embodiment of the process a very particularly preferred reactor is selected from a screw reactor, a rotary oven or fluidized bed. Further reactors preferred for the process according to the invention and embodiments thereof are described in the embodiments of the pyrolysis device of the invention and in an embodiment of the process with the use of a catalyst (vide infra).

According to the invention, the pyrolysis feedstock introduced into the reactor includes at least one material comprising a mixture of polycarbonate-containing compound and polystyrene-containing compound.

In one embodiment of the process according to the invention, said pyrolysis feedstock contains said material in a total amount of 10.0% to 80.0% by weight, more preferably 30.0% to 70.0% by weight, in each case based on the total weight of the pyrolysis feedstock.

It has been found to be advantageous when said material of the pyrolysis feedstock is preferably introduced into the reactor in the form of solid particles (especially in the form of a granular mixture). A granular mixture of said material is formed from a multitude of loose, solid particles of said material, which in turn comprise what are known as grains. A grain is a term for the particulate constituents of powders (grains are the loose, solid particles), dusts (grains are the loose, solid particles), granules (loose, solid particles are agglomerates of several grains), and other granular mixtures. The flowability of a granular mixture relates to its ability to flow freely under its own weight from a pour test funnel having an outlet 16.5 mm in diameter.

The solid particles, more particularly the loose, solid particles of the granular mixture of said material introduced into the reactor, preferably have an average diameter $X_{50.3}$ (volume average) of from 0.01 mm to 5 cm, preferably from 0.1 mm to 5 cm. The average particle size diameter $X_{50.3}$ is determined by sieving or using a Camsizer particle size analyzer from Retsch.

Said material can generally be, for example, a homopolymer, a copolymer, a comb polymer, a block polymer or mixtures thereof.

Said materials of this kind are particularly suitable when, in addition to said polystyrene-containing compound as poly carbonate-containing compound, at least one compound is present that contains at least ten

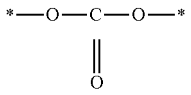

structural units, where * denotes a valence of the polymer backbone.

Polycarbonate-containing compounds for said materials that are suitable for the process of the invention are for example aromatic polycarbonates and/or aromatic polyestercarbonates. These are known from the literature or can be produced by processes known from the literature (for the production of aromatic polycarbonates see for example Schnell, "Chemistry and Physics of Polycarbonates", Interscience Publishers, 1964, and also DE-AS 1 495 626, DE-A 2 232 877, DE-A 2 703 376, DE-A 2 714 544, DE-A 3 000 610, DE-A 3 832 396; for production of aromatic polyestercarbonates see for example DE-A 3 007 934).

The aromatic polycarbonate usable as a polycarbonate-containing compound is prepared for example by reacting compounds having at least two hydroxyl groups, especially diphenols, with carbonyl halides, preferably phosgene and/or with aromatic dicarboxylic acid dihalides, preferably dihalides of benzenedicarboxylic acid, by the interfacial process, optionally using chain terminators, for example monophenols, and optionally using trifunctional or more than trifunctional branching agents, for example triphenols or tetraphenols. Also possible is production via a melt polymerization process by reaction of compounds having at least two hydroxyl groups, especially diphenols, with for example diphenyl carbonate.

According to the invention, it is possible to advantageously use said materials of this kind in which the polycarbonate-containing compound is at least one compound obtained by reacting at least the compounds (i) at least one aromatic compound having at least two hydroxyl groups, particularly preferably bisphenol A, and (ii) phosgene or diphenyl carbonate.

For the production of the poly carbonate-containing compound it is preferable to use at least one aromatic compound having at least two hydroxyl groups that is selected from the general formula (I), (I)

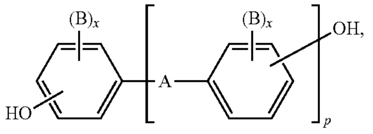

where

A is a single bond, $C_1$ to $C_5$ alkylene, $C_2$ to $C_5$ alkylidene, $C_5$ to $C_6$ cycloalkylidene, —O—, —SO—, —CO—, —S—, —$SO_2$—, $C_6$ to $C_{12}$ arylene, onto which further aromatic rings optionally containing heteroatoms may be fused, or a radical of formula (II) or (III)

(II)

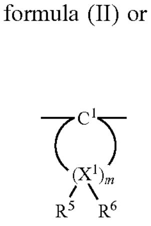

(III)

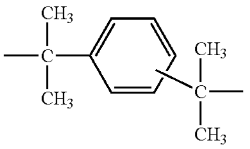

B is in each case $C_1$ to $C_{12}$ alkyl, preferably methyl, halogen, preferably chlorine and/or bromine, x is in each case independently 0, 1 or 2, p is 1 or 0, and $R^5$ and $R^6$ can be selected individually for each $X^1$ and are each independently hydrogen or $C_1$ to $C_6$ alkyl, preferably hydrogen, methyl or ethyl, $X^1$ is carbon and m is an integer from 4 to 7, preferably 4 or 5, with the proviso that, on at least one atom $X^1$, $R^5$ and $R^6$ are both alkyl.

Preferred aromatic compounds having at least two hydroxyl groups are hydroquinone, resorcinol, dihydroxydiphenols, bis(hydroxyphenyl)-$C_1$ to -$C_5$ alkanes, bis(hydroxyphenyl)-$C_5$ to -$C_6$ cycloalkanes, bis(hydroxyphenyl) ethers, bis(hydroxyphenyl) sulfoxides, bis(hydroxyphenyl) ketones, bis(hydroxyphenyl) sulfones and α,α-bis(hydroxyphenyl)diisopropylbenzenes, and ring-brominated and/or ring-chlorinated derivatives thereof.

Particularly preferred aromatic compounds having at least two hydroxyl groups are 4,4'-dihydroxybiphenyl, bisphenol A, 2,4-bis(4-hydroxyphenyl)-2-methylbutane, 1,1-bis(4-hydroxyphenyl)cyclohexane, 1,1-bis(4-hydroxyphenyl)-3,3,5-trimethylcyclohexane, 4,4'-dihydroxydiphenyl sulfide, 4,4'-dihydroxydiphenyl sulfone, and also the di- and tetrabrominated or chlorinated derivatives thereof, for example 2,2-bis(3-chloro-4-hydroxyphenyl)propane, 2,2-bis(3,5-dichloro-4-hydroxyphenyl)propane or 2,2-bis(3,5-dibromo-4-hydroxyphenyl)propane. Particular preference is given to 2,2-bis(4-hydroxyphenyl)propane (bisphenol A).

The aromatic compounds having at least two hydroxyl groups may be used individually or as any desired mixtures. The aromatic compounds having at least two hydroxyl groups are known from the literature or can be obtained by methods known from the literature.

Examples of chain terminators suitable for the production of thermoplastic aromatic polycarbonates include phenol, p-chlorophenol, p-tert-butylphenol or 2,4,6-tribromophenol, and also long-chain alkylphenols such as 4-[2-(2,4,4-trimethylpentyl)]phenol, 4-(1,3-tetramethylbutyl)phenol according to DE-A 2 842 005 or monoalkylphenols or dialkylphenols having a total of 8 to 20 carbon atoms in the alkyl substituents, for example 3,5-di-tert-butylphenol, p-isooctylphenol, p-tert-octylphenol, p-dodecylphenol, and 2-(3,5-dimethylheptyl)phenol and 4-(3,5-dimethylheptyl)phenol. The amount of chain terminators to be used is generally between 0.5 mol % and 10 mol % based on the molar sum of the aromatic compounds having at least two hydroxyl groups used in each case.

In a preferred embodiment of the invention, employable thermoplastic aromatic polycarbonates have average molecular weights (weight-average MW, measured by GPC (gel-permeation chromatography) using a polycarbonate standard based on bisphenol A) of preferably 20000 to 40000 g/mol, more preferably 24000 to 32000 g/mol, particularly preferably 26000 to 30000 g/mol.

The thermoplastic aromatic polycarbonates may be branched in a known manner and preferably through incorporation of 0.05 to 2.0 mol %, based on the sum total of aromatic compound having at least two hydroxyl groups used, of trifunctional or more than trifunctional compounds, for example ones having three or more phenolic groups.

Preference is given to using linear polycarbonates, more preferably ones based on bisphenol A.

Both homopolycarbonates and copolycarbonates are suitable. For the production of copolycarbonates employable with preference according to the invention it is also possible to use 1% to 25% by weight, preferably 2.5% to 25% by weight, based on the total amount of aromatic compound having at least two hydroxyl groups to be used, of polydiorganosiloxanes having hydroxyaryloxy end groups. These are known (U.S. Pat. No. 3,419,634) and may be produced by processes known from the literature. Likewise suitable are polydiorganosiloxane-containing copolycarbonates; the production of polydiorganosiloxane-containing copolycarbonates is described for example in DE-A 3 334 782.

Aromatic dicarboxylic acid dihalides for the production of aromatic polyestercarbonates are preferably the diacid dichlorides of isophthalic acid, terephthalic acid, diphenyl ether 4,4'-dicarboxylic acid, and naphthalene-2,6-dicarboxylic acid.

Particular preference is given to mixtures of the diacid dichlorides of isophthalic acid and terephthalic acid in a ratio of between 1:20 and 20:1.

In the production of polyestercarbonates, a carbonyl halide, preferably phosgene, is also additionally used as a bifunctional acid derivative.

Useful chain terminators for the production of aromatic polyestercarbonates include, aside from the monophenols already mentioned, the chloroformic esters thereof and the acid chlorides of aromatic monocarboxylic acids, which may optionally be substituted by $C_1$ to $C_{22}$ alkyl groups or by halogen atoms, and aliphatic $C_2$ to $C_{22}$ monocarboxylic acid chlorides.

The amount of chain terminators is in each case 0.1 to 10 mol %, based on moles of aromatic compound having at least two hydroxyl groups in the case of phenolic chain terminators and on moles of dicarboxylic acid dichloride in the case of monocarboxylic acid chloride chain terminators.

In the production of aromatic polyestercarbonates it is also possible to use one or more aromatic hydroxycarboxylic acids.

The aromatic polyestercarbonates may be linear or they may be branched in a known manner (see DE-A 2 940 024 and DE-A 3 007 934), preference being given to linear polyestercarbonates.

Branching agents used may for example be tri- or polyfunctional carboxylic acid chlorides, such as trimesyl trichloride, cyanuric trichloride, 3,3',4,4'-benzophenonetetracarboxylic acid tetrachloride, 1,4,5,8-naphthalenetetracarboxylic acid tetrachloride or pyromellitic tetrachloride, in amounts of 0.01 to 1.0 mol % (based on dicarboxylic acid dichlorides used), or tri- or polyfunctional phenols, such as phloroglucinol, 4,6-dimethyl-2,4,6-tri(4-hydroxyphenyl)hept-2-ene, 4,6-dimethyl-2,4,6-tri(4-hydroxyphenyl)heptane, 1,3,5-tri(4-hydroxyphenyl)benzene, 1,1,1-tri(4-hydroxyphenyl)ethane, tri(4-hydroxyphenyl)phenylmethane, 2,2-bis[4,4-bis(4-hydroxyphenyl)cyclohexyl]propane, 2,4-bis(4-hydroxyphenylisopropyl)phenol, tetra(4-hydroxyphenyl)methane, 2,6-bis(2-hydroxy-5-methylbenzyl)-4-methylphenol, 2-(4-hydroxyphenyl)-2-(2,4-dihydroxyphenyl) propane, tetra(4-[4-hydroxyphenylisopropyl]phenoxy) methane, 1,4-bis[4,4'-dihydroxytriphenyl)methyl]benzene, in amounts of 0.01 to 1.0 mol %, based on diphenols used. Phenolic branching agents may be initially charged together with the diphenols; acid chloride branching agents may be introduced together with the acid dichlorides.

The proportion of carbonate structural units in the thermoplastic aromatic polyestercarbonates may be varied as desired. Preferably, the proportion of carbonate groups is up to 100 mol %, especially up to 80 mol %, more preferably up to 50 mol %, based on the sum total of ester groups and carbonate groups. Both the ester fraction and the carbonate fraction of the aromatic polyestercarbonates may be present in the form of blocks or in random distribution in the polycondensate.

The aromatic polycarbonates and polyestercarbonates may be used alone or in any desired mixture in said material of the process according to the invention.

Said material of the pyrolysis feedstock comprises in addition to at least one polycarbonate-containing compound at least one polystyrene-containing compound.

In the context of the present application, “polystyrene-containing material” is understood as meaning a compound, preferably a polymer, containing structural units derived from styrene or styrene derivatives, especially from styrene.

“Polystyrene-containing compound” is thus according to the invention understood as meaning a compound containing a repeat unit derived from styrene optionally substituted on the aromatic ring (such as styrene, α-methylstyrene, p-methylstyrene, p-chlorostyrene in particular). In one embodiment of the process according to the invention, it is advantageous when material is used in the pyrolysis feedstock that in addition to at least one polycarbonate-containing compound comprises at least one polymer in the form of a polystyrene-containing compound having at least ten repeat units of the formula $$*—CR^1Ph\text{-}CH_2—*$$

where * denotes a valence of the repeat unit of the polymer backbone, $R^1$ is a hydrogen atom or a methyl group, and Ph is a phenyl group optionally substituted with at least one group selected from $C_1$ to $C_4$ alkyl group and halogen atom (especially chlorine). Said material particularly preferably comprises in addition to at least one polycarbonate-containing compound at least one polymer in the form of a polystyrene-containing compound having at least ten repeat units of the above formula that are derived from styrene ($R^1$=H, Ph=phenyl), α-methylstyrene ($R^1$=methyl, Ph=phenyl), p-methylstyrene ($R^1$=H, Ph=4-methylphenyl), p-chlorostyrene ($R^1$=H, Ph=4-chlorophenyl) or mixtures thereof.

As a material employable with preference according to the invention, as well as at least one polycarbonate-containing compound it additionally comprises as a polystyrene-containing compound at least one polymer selected from rubber-modified graft polymers (B1) having structural units derived from styrene or styrene derivatives or rubber-free vinyl (co)polymers having structural units (B2) derived from styrene or styrene derivatives, or a mixture of two or more such polymers.

Such rubber-modified graft polymers (B1) used with preference comprise

B.1.1 5% to 95% by weight, preferably 15% to 92% by weight, especially 25% to 60% by weight, based on component B.1, of vinylaromatics and/or ring-substituted vinylaromatics (such as styrene, α-methylstyrene, p-methylstyrene, p-chlorostyrene) on B.1.2 95% to 5% by weight, preferably 85% to 8% by weight, especially 75% to 40% by weight, based on component B.1, of one or more rubber-like graft bases, preferably having glass transition temperatures of <10° C., more preferably <0° C., especially preferably <−20° C.

The glass transition temperature is measured by differential scanning calorimetry (DSC) in accordance with standard DIN EN 61006 at a heating rate of 10 K/min, $T_g$ being defined as the midpoint temperature (tangent method).

The graft base B.1.2 generally has a median particle size ($d_{50}$) of from 0.05 to 10 μm, preferably 0.1 to 5 μm, more preferably 0.2 to 1 μm. The median particle size $d_{50}$ is the diameter above and below which 50% each by weight of the particles are found. It can be determined by ultracentrifuge measurement (W. Scholtan, H. Lange, Kolloid, Z. und Z. Polymere 250 (1972), 782-1796).

Monomers B.1.1 are preferably mixtures of

B.1.1.1 50 to 99, preferably 60 to 80, especially 70 to 80, parts by weight, based on B.1.1, of vinylaromatics and/or ring-substituted vinylaromatics (selected in particular from styrene, α-methylstyrene, p-methylstyrene, p-chlorostyrene or mixtures thereof), and B.1.1.2 1 to 50, preferably 20 to 40, especially 20 to 30, parts by weight, based on B.1.1, of vinyl cyanides (unsaturated nitriles such as acrylonitrile and methacrylonitrile) and/or $C_1$-$C_8$ alkyl (meth)acrylates, such as methyl methacrylate, n-butyl acrylate, tert-butyl acrylate, and/or derivatives (such as anhydrides and imides) of unsaturated carboxylic acids, for example maleic anhydride and N-phenylmaleimide.

Preferred monomers B.1.1.1 are selected from at least one of the monomers styrene and α-methylstyrene; preferred monomers B.1.1.2 are selected from at least one of the monomers acrylonitrile, maleic anhydride, and methyl methacrylate. Particularly preferred monomers are styrene as B.1.1.1 and acrylonitrile as B.1.1.2.

Examples of graft bases B.1.2 suitable for the graft polymers B.1 are diene rubbers, EP(D)M rubbers, i.e. rubbers based on ethylene/propylene and optionally diene, acrylate rubbers, polyurethane rubbers, silicone rubbers, chloroprene rubbers, and ethylene/vinyl acetate rubbers, and also silicone/acrylate composite rubbers.

Preferred graft bases B.1.2 are diene rubbers, for example based on butadiene and isoprene, or mixtures of diene rubbers or copolymers of diene rubbers or mixtures thereof with further copolymerizable monomers (for example according to B.1.1.1 and B.1.1.2).

Particularly preferred as graft substrate B.1.2 is pure polybutadiene rubber.

Particularly preferred as polymer B1 are for example polymers selected from acrylonitrile-butadiene-styrene copolymer (also referred to as ABS polymer) or methacrylate-butadiene-styrene copolymer (also referred to as MBS polymer), as described for example in DE-A 2 035 390 (=U.S. Pat. No. 3,644,574) or in DE-A 2 248 242 (=GB-A 1 409 275), or in Ullmanns Enzyklopadie der technischen Chemie [Ullmann's Encyclopedia of Industrial Chemistry], vol. 19 (1980), p. 280 ff.

The graft copolymers B.1 are produced by free-radical polymerization, for example by emulsion, suspension, solution or bulk polymerization, preferably by emulsion or bulk polymerization.

The gel content of the graft base B.1.2 is at least 30% by weight, preferably at least 40% by weight, especially at least 60% by weight, in each case based on B.1.2 and measured as insoluble fraction in toluene.

The gel content of the graft base B.1.2 is determined at 25° C. in a suitable solvent as the content insoluble in these solvents (M. Hoffmann, H. Kromer, R. Kuhn, Polymeranalytik I und II, Georg Thieme-Verlag, Stuttgart 1977).

Particularly suitable graft rubbers are also ABS polymers produced by redox initiation with an initiator system composed of organic hydroperoxide and ascorbic acid according to U.S. Pat. No. 4,937,285.

Since the graft monomers are known to not necessarily be completely grafted onto the graft base in the grafting reaction, graft polymers B.1 are in accordance with the invention understood also to include products that result from (co) polymerization of the graft monomers in the presence of the graft base and are among the products obtained during workup. These products may accordingly also comprise free (co)polymer of the graft monomers, i.e. (co)polymer not chemically bonded to the rubber.

Monomers having more than one polymerizable double bond may be copolymerized for crosslinking purposes. Preferred examples of crosslinking monomers are esters of unsaturated monocarboxylic acids having 3 to 8 carbon atoms and unsaturated monohydric alcohols having 3 to 12 carbon atoms or saturated polyols having 2 to 4 OH groups and 2 to 20 carbon atoms, such as ethylene glycol dimethacrylate and allyl methacrylate; polyunsaturated heterocyclic compounds, such as trivinyl and triallyl cyanurate; polyfunctional vinyl compounds, such as di- and trivinylbenzenes; but also triallyl phosphate and diallyl phthalate. Preferred crosslinking monomers are allyl methacrylate, ethylene glycol dimethacrylate, diallyl phthalate, and heterocyclic compounds having at least three ethylenically unsaturated groups. Particularly preferred crosslinking monomers are the cyclic monomers triallyl cyanurate, triallyl isocyanurate, triacryloylhexahydro-s-triazine, and triallylbenzenes. The amount of the crosslinked monomers is preferably 0.02% to 5% by weight, especially 0.05% to 2% by weight, based on the graft base B.1.2. In the case of cyclic crosslinking monomers having at least three ethylenically unsaturated groups, it is advantageous to limit the amount to below 1% by weight of the graft base B.1.2.

Preferred "other" polymerizable, ethylenically unsaturated monomers that, alongside the acrylic esters, may optionally be used for the preparation of the graft base B.1.2 are for example acrylonitrile, styrene, α-methylstyrene, acrylamides, vinyl $C_1$-$C_6$ alkyl ethers, methyl methacrylate, and butadiene. Preferred acrylate rubbers as graft base B.1.2 are emulsion polymers having a gel content of at least 60% by weight.

Other suitable graft substrates according to B.1.2 are silicone rubbers having graft-active sites, such as are described in DE-A 3 704 657, DE-A 3 704 655, DE-A 3 631 540, and DE-A 3 631 539.

The rubber-free vinyl (co)polymers according to component B.2 are preferably rubber-free homopolymers and/or copolymers of at least one monomer from the group comprising vinylaromatics, vinyl cyanides (unsaturated nitriles), $C_1$ to $C_8$ alkyl (meth)acrylates, unsaturated carboxylic acids, and derivatives (such as anhydrides and imides) of unsaturated carboxylic acids.

Especially suitable are (co)polymers B.2 from

B.2.1 10% to 100% by weight, preferably 50% to 99% by weight, more preferably 60% to 80% by weight, especially 70% to 80% by weight, in each case based on the total weight of (co)polymer B.2, of at least one monomer selected from the group comprising vinylaromatics (for example styrene, α-methylstyrene) and ring-substituted vinylaromatics (for example p-methylstyrene, p-chlorostyrene) and B.2.2 0% to 90% by weight, preferably 1% to 50% by weight, more preferably 20% to 40% by weight, especially 20% to 30% by weight, in each case based on the total weight of (co)polymer B.2, of at least one monomer selected from the group comprising vinyl cyanides for example unsaturated nitriles such as acrylonitrile and methacrylonitrile, $C_1$-$C_8$ alkyl (meth)acrylates, for example methyl methacrylate, n-butyl acrylate, and tert-butyl acrylate, unsaturated carboxylic acids, and derivatives of unsaturated carboxylic acids, for example maleic anhydride and N-phenylmaleimide.

These (co)polymers B.2 are resinous, thermoplastic, and rubber-free. Said material especially preferably comprises at least the copolymer of B.2.1 styrene and B.2.2 acrylonitrile and/or the homopolymer of B.2.1.

(Co)polymers B.2 of this kind are known and can be produced by free-radical polymerization, especially by emulsion, suspension, solution or bulk polymerization. The (co)polymers have average molecular weights MW (weight average, determined by GPC with polystyrene as standard) preferably of between 15000 and 250000 g/mol, preferably in the range from 80 000 to 150 000 g/mol.

Said material of the pyrolysis feedstock may in addition to at least one polycarbonate-containing compound and at least one polystyrene-containing compound additionally comprise at least one polymer additive selected from flame retardants, anti-drip agents, flame retardant synergists, smoke inhibitors, lubricants and demolding agents, nucleating agents, antistats, conductivity additives, stabilizers (for example hydrolysis, heat aging and UV stabilizers and also transesterification inhibitors), flow promoters, phase compatibilizers, further polymeric constituents other than components A and B (for example functional blend partners), fillers and reinforcers, and dyes and pigments.

It was also found that an increased content of aromatic compound having at least two hydroxyl groups in the pyrolysis product can be obtained, and thus recovered, when the pyrolysis feedstock is limited to a low content of phosphorus-containing organic compounds or is even free of such compounds. Appropriate as such a defined total amount of phosphorus-containing organic compound has been found to be a proportion contributed by this total amount and based on the total weight of the pyrolysis feedstock of from 0% by weight to not more than 0.5% by weight of phosphorus, preferably from 0% by weight to not more than 0.1% by weight of phosphorus, more preferably from 0% by weight to not more than 0.05% by weight of phosphorus, and particularly preferably from 0% by weight to not more than 0.01% by weight of phosphorus. The technical effect resulting from this defined total amount was also achieved for a pyrolysis feedstock comprising at least one polycarbonate-containing compound and a correspondingly limited total amount of phosphorus-containing organic compound, and optionally additionally at least one polystyrene-containing compound.

A further embodiment of the process according to the invention is therefore a process that according to step (a) is characterized in that the pyrolysis feedstock comprises at least one polycarbonate-containing compound and a defined total amount of phosphorus-containing organic compound such that, based on the total weight of the pyrolysis feedstock, the proportion contributed by this total amount of phosphorus-containing organic compound is from 0% by weight to not more than 0.5% by weight of phosphorus, preferably from 0% by weight to not more than 0.10% by weight of phosphorus, more preferably from 0% by weight to not more than 0.05% by weight of phosphorus, and particularly preferably from 0% by weight to not more than 0.01% by weight of phosphorus and optionally at least one polystyrene-containing compound.

It is further preferable when, for a concomitant recovery of styrene and derivatives thereof, the pyrolysis feedstock includes at least material comprising a mixture of polycarbonate-containing compound and polystyrene-containing compound and said total amount of phosphorus-containing organic compound.

In a further embodiment, it has been found to be preferable in accordance with the invention when the phosphorus-containing organic compound that may be present only in a limited amount is selected from phosphorus-containing organic compounds in which phosphorus has a formal oxidation state of +5.

It has additionally been found to be particularly preferable when the pyrolysis feedstock is free from phosphorus-containing organic compounds in which at least one phosphorus atom has a formal oxidation state of +5.

The phosphorus-containing organic compounds that may be present only in a limited amount are preferably selected from at least one compound of the group consisting of organic phosphoric esters, organic phosphonic esters, organic phosphazenes, and phosphonate amines, especially organic phosphoric esters and organic phosphonic esters. Said phosphorus-containing organic compound is particularly preferably selected from at least one compound of the group consisting of organic phosphoric acid monoesters, organic phosphoric acid diesters, organic phosphoric acid triesters, and oligomeric phosphoric esters. It is thus possible to employ mixtures of more than one of these compounds, which may likewise be present only in a limited amount.

The abovementioned phosphonate amines and phosphazenes that in the preferred embodiment may be present in the pyrolysis feedstock only in a limited amount may be for example those described in WO 00/00541 and WO 01/18105.

Particularly preferred phosphorus-containing organic compounds that may be present only in a limited amount are for the purposes of the present invention compounds of the general formula (IV)

(IV)

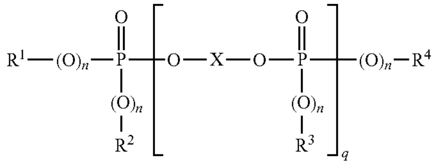

where $R^1$, $R^2$, $R^3$, and $R^4$ are each independently optionally halogenated C1 to C8 alkyl, in each case optionally substituted by alkyl, preferably C1 to C4 alkyl, and/or halogen, preferably chlorine or bromine, substituted C5 to C6 cycloalkyl, C6 to C20 aryl or C7 to C12 aralkyl, n is independently 0 or 1, q is 0 to 30, and X is a multiring aromatic radical having 12 to 30 carbon atoms, or a linear or branched aliphatic radical having 2 to 30 carbon atoms, which may be OH-substituted and may contain up to eight ether bonds.

Preferably, $R^1$, $R^2$, $R^3$, and $R^4$ in the formula (IV) are each independently C1 to C4 alkyl, phenyl, naphthyl or phenyl-C1 alkyl to phenyl-C4 alkyl. The aromatic groups $R^1$, $R^2$, $R^3$, and $R^4$ may in turn be substituted by halogen and/or alkyl groups, preferably chlorine, bromine and/or C1 to C4 alkyl. Particularly preferred aryl radicals are cresyl, phenyl, xylenyl, propylphenyl or butylphenyl and also the corresponding brominated and chlorinated derivatives thereof.

X in the formula (IV) is preferably a multiring aromatic radical having 12 to 30 carbon atoms. This is preferably derived from aromatic compounds having at least two hydroxyl groups of the general formula (I).

n in the formula (IV) may independently be 0 or 1, preferably n is 1.

q has integer values of from 0 to 30, preferably 0 to 20, more preferably 0 to 10, or in the case of mixtures has average values of from 0.8 to 5.0, preferably 1.0 to 3.0, further preferably 1.05 to 2.00 and especially preferably 1.08 to 1.60.

X in formula (IV) particularly preferably represents

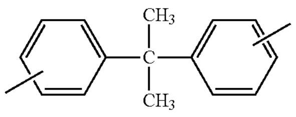

,

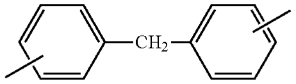

,

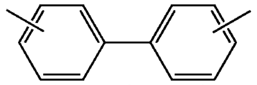

,

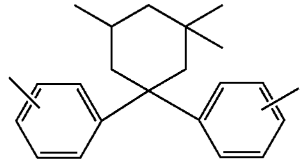

or chlorinated or brominated derivatives thereof, in particular, X is derived from bisphenol A or diphenylphenol. X is particularly preferably derived from bisphenol A.

Phosphorus compounds of the formula (IV) are especially tributyl phosphate, triphenyl phosphate, tricresyl phosphate, diphenyl cresyl phosphate, diphenyl octyl phosphate, diphenyl 2-ethylcresyl phosphate, tri(isopropylphenyl) phosphate, and bisphenol A-bridged oligophosphate. The use of oligomeric phosphoric esters of the formula (IV) that are derived from bisphenol A is especially preferred.

As the phosphorus-containing organic compound that may be present only in a limited amount, greatest preference is given to using the bisphenol A-based oligophosphate shown in formula (IVa)

(IVa)

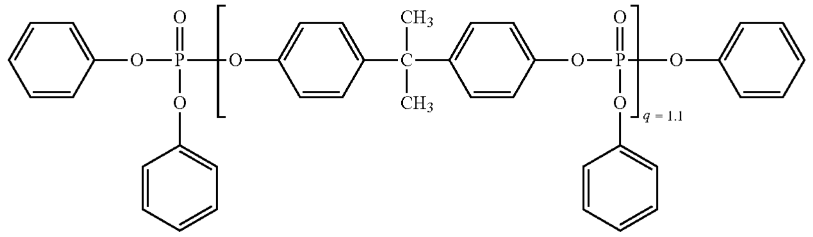

The abovementioned phosphorus organic compounds are known (see for example EP-A 363 608, EP-A 640 655) or can be prepared in an analogous manner by known methods (for example Ullmanns Enzyklopadie der technischen Chemie [Ullmann's Encyclopedia of Industrial Chemistry], vol. 18, p. 301 ff. 1979; Houben-Weyl, Methoden der organischen Chemie [Methods of Organic Chemistry], vol. 12/1, p. 43; Beilstein vol. 6, p. 177).

As phosphorus-containing organic compounds suitable according to the invention that may be present only in a limited amount, it is possible to use for example also mixtures of organic phosphoric esters having different chemical structures and/or having the same chemical structure and different molecular weights.

When employing oligomeric phosphoric esters as the phosphorus-containing organic compound that may be present only in a limited amount, preference is given to using mixtures having the same structure and different chain lengths, the q value shown in formulas (IV) and (IVa) being the average q value. The average q value is determined by using high-pressure liquid chromatography (HPLC) at 40° C. in a mixture of acetonitrile and water (50:50) to determine the composition of the phosphorus compound (molecular weight distribution) and calculating therefrom the average values for q.

In a preferred embodiment the composition comprises pentaerythritol tetrastearate as a demolding agent.

The metering and processibility of the pyrolysis feedstock in the pyrolysis of the process of the invention can be simplified by said pyrolysis feedstock in step (a) also comprising in addition to said material at least one filler. Said filler preferably does not catalyze the thermal breakdown of polycarbonate during the pyrolysis. It is in turn particularly preferable when the filler is at least one metal oxide not catalytically active in the pyrolysis in the thermal breakdown of polycarbonate that preferably selected from $SiO_2$.

The polycarbonate material is preferably mixed with a filler, for example sand, thereby making continuous process control of the process according to the invention simpler. In particular, sticking of said material in the reactor and in the supply of the metering device to the reactor is avoided. In one embodiment, the filler and said material are supplied to the pyrolysis feedstock as a mixture in a volume ratio of filler to said material of at least 0.1:1 to 10:1.

Catalysts may be used to make the pyrolysis process more selective and more efficient. More effective and more selective breakdown is obtained when, in one embodiment of the process according to the invention, said pyrolysis feedstock introduced in step (a) also comprises in addition to said material at least one catalyst influencing the breakdown reaction of said material. A suitable catalyst can lower the pyrolysis temperature, reduce the spectrum of products to the desired products and optionally minimize carbonization.

For an efficient process, inexpensive catalysts are preferred. These can be for example naturally occurring materials such as inorganic salts, refractory oxides, minerals, and industrial stones into which ions can optionally be exchanged in a simple ion-exchange process, since they do not require extensive synthesis. They are readily available and therefore relatively cheap. Synthetic catalysts such as zeolites (for example of types ZSM-5, A, X, Y, etc.) are on the other hand an example of catalysts that, although effective, are not cheap, since they have to be specially manufactured.

In addition to the function as a catalyst, catalysts can also simplify the metering and processibility of the pyrolysis feedstock in the pyrolysis. When using a catalyst, the amount of filler used can in this case be reduced. In one embodiment, the total amount of filler and catalyst is supplied to the pyrolysis feedstock as a mixture in a ratio to the amount of said material in a volume ratio of at least 0.1:1 to 10:1.

In the pyrolysis reaction, preferably at least one catalyst is selected from the group consisting of alkaline inorganic materials, more preferably from the group of naturally occurring materials defined above. These inorganic materials may be refractory oxides. Refractory oxides are metal oxides that are stable at high temperatures from 300° C. to 700° C. Such oxides that function as catalysts include the oxides of aluminum, magnesium, zirconium, titanium, chromium, zinc, tin, and other metals or combinations of aluminum oxide with magnesium oxide and/or calcium oxide. Crystalline inorganic materials include aluminosilicates, silicon aluminum phosphates, silicalite, spinels, and other natural zeolites and clays. Especially suitable as said catalyst is thus at least one compound from the group consisting of inorganic salts, minerals, metal oxides, mixed oxides, clays, and zeolites.

It is possible to use both homogeneous and heterogeneous catalysts. However, preferred embodiments of the process according to the invention are those in which the catalyst is a heterogeneous catalyst. It has been found to be advantageous when the catalyst is introduced into the reactor preferably in the form of solid particles (especially in the form of a granular mixture). The heterogeneous catalyst used particularly preferably has an average particle size in the solid particles thereof, more particularly in the loose, solid particles of the granular mixture thereof, an average diameter $X_{50.3}$ (volume average) of from 0.01 mm to 5 cm, preferably from 0.1 mm to 5 cm. The average particle size diameter $X_{50.3}$ is determined by sieving or using a Camsizer particle size analyzer from Retsch.

When using a heterogeneous catalyst, it has in a further preferred embodiment been found to be particularly suitable when the catalyst particles have a smaller or the same particle size as the particles of said material. It is therefore preferable when the average particle size of the catalyst present in the pyrolysis feedstock corresponds at most to the average particle size of said material present therein.

As a suitable said catalyst that is particularly preferred, the pyrolysis feedstock may comprise at least one basic catalyst. In the case of a solid basic catalyst, the number and strength of the basic centers in the catalyst can be determined by Fourier transform infrared spectroscopy and temperature-programmed desorption of $CO_2$ (TPD-CO2), or determined using standard titrimetric methods.

If a catalyst is added, it can be admixed with the filler, coated onto the filler, or used as a substitute for the filler.

Since the catalyst used in the process according to the invention tends to form deposits of carbonized material and other carbon residues, when using a catalyst it is preferable to use a reactor that readily and preferably allows the catalyst to be discharged and continuously regenerated. Therefore, the use of a continuous stirred-tank reactor (CSTR), moving bed, screw reactor, screw-conveyor reactor, entrained-flow reactor, rotating-cone reactor, or fluidized-bed reactor is preferred over the use of a fixed-bed reactor.

The deactivated catalyst (deactivated for example through carbonization) is present in the pyrolysis residue and, after discharge of the pyrolysis residue from the reactor, can be supplied to a regenerator and after regeneration added to the pyrolysis feedstock of step (b) to be introduced into the pyrolysis reactor. Reactors that permit a short contact time, intensive mixing of the components in the feedstream with the catalyst, and continuous recycling of the regenerated catalyst to the pyrolysis zone are most preferred. Since this is the case with a screw reactor, rotary oven or fluidized bed, these reactors are particularly preferred.

The pyrolysis feedstock introduced into the reactor in step (a) is at least partially broken down according to step (b), with the formation of pyrolysate and pyrolysis residue.

After being introduced into the reactor, the pyrolysis feedstock is heated to a temperature in the range from 300° C. to 700° C. A particularly successful improvement of the result of the process according to the invention can be achieved when, in one embodiment, the introduced pyrolysis feedstock is temperature-controlled at 300° C. to 700° C. and, on reaching this target temperature, the residence time of the correspondingly temperature-controlled pyrolysis feedstock until the time of discharge of the pyrolysis residue resulting therefrom is from 1 second to 2 hours, preferably between 2 minutes and 60 minutes, the temperature and the content of oxygen gas in the reactor during this time being the values defined in step (b).

When the pyrolysis feedstock in the process according to the invention includes a catalyst, this catalyst is present in the pyrolysis residue that is discharged. In a further embodiment of the process, the discharged pyrolysis residue as described above is therefore supplied to a step for regeneration of the catalyst contained therein.

Independently thereof, good results can be achieved when the discharge of the pyrolysate from the reactor that takes place in step (b) is ensured by a gas stream passed through the reactor or by suction, and more preferably by the residence time of the pyrolysate, as the period between the time of introduction of said material introduced into the reactor in step (a) and the time of discharge of the pyrolysate, being from 0.1 seconds to 10 seconds, preferably between 0.5 seconds and 5 seconds, more preferably 0.5 seconds to 2 seconds.

If a gas stream is passed through the reactor for this purpose, an inert gas preferably selected from nitrogen, argon, $CO_2$, NO or a mixture thereof is particularly suitable as the gas for this gas stream.

If a gas stream is used to discharge the pyrolysate, it is preferable according to the invention when the flow rate of the gas stream in the reactor, as the superficial velocity, is in the range from 0.01 m/s to 20 m/s. If a fixed-bed reactor is chosen as the reactor, it is preferable according to the invention when the flow rate of the gas stream in the reactor, as the superficial velocity, is in the range from 0.03 m/s to 1 m/s. If a fluidized-bed reactor is chosen as the reactor, it is preferable according to the invention the flow rate of the gas stream in the reactor, as the superficial velocity, is in the range from 0.5 m/s to 2 m/s. If an entrained-flow reactor is chosen as the reactor, it is preferable according to the invention the flow rate of the gas stream in the reactor, as the superficial velocity, is in the range from 5 m/s to 20 m/s.

As the conditions of the invention for the breakdown in the pyrolysis in step (b), the temperature in the reactor is 300 to 700° C. and the amount of oxygen gas in the reactor is from 0% to 2.0% by volume based on the total volume of the gases present in the reactor.

The amount of oxygen gas according to the invention is established by filling the reactor packed with said material of said pyrolysis feedstock with inert gas, in particular with nitrogen, argon, $CO_2$, NO or a mixture thereof. The inert gas may additionally be admixed with reactive gases other than oxygen gas, in particular gases selected from methane, gaseous $H_2O$, hydrogen gas or mixtures thereof.

To minimize the ingress of oxygen gas due to the introduction of the pyrolysis feedstock into the reactor, the pyrolysis feedstock can be freed from oxygen gas before it is introduced in step (a), for example by driving out the oxygen gas by stripping with a stripping gas, for example in a storage vessel upstream of the reactor. For example, an inert gas, more particularly nitrogen, argon, $CO_2$, NO or mixtures thereof, could in the storage vessel be passed as a stripping gas from above or from below (preferably from above) via a frit into the vessel and into the pyrolysis feedstock so as to drive out the oxygen gas.

In a preferred embodiment of the process according to the invention, the temperature in step (b) is from 350° C. to 650° C., preferably between 400° C. and 650° C., particularly preferably from 420° C. to 600° C., very particularly preferably from 450° C. to 580° C.

In a further preferred embodiment of the process according to the invention, the amount of oxygen gas in the reactor in step (b) is not more than 0.5% by volume, preferably 0.1% by volume, in each case based on the total volume of the gases present in the reactor.

In a very preferred embodiment of the process according to the invention, firstly the temperature in step (b) is from 350° C. to 650° C., preferably between 400° C. and 650° C., particularly preferably from 420° C. to 600° C., very particularly preferably from 450° C. to 580° C., and secondly the amount of oxygen gas in the reactor is not more than 0.5% by volume, preferably 0.10% by volume, in each case based on the total volume of the gases present in the reactor.

A preferred embodiment of the process provides continuous process control. For this, at least steps (a) and (b) run concomitantly in the context of continuous process control.

The pyrolysis product obtained according to step (c) can be worked up using standard separation methods, thereby affording (i) at least one aromatic compound having at least two hydroxyl substituents, preferably bisphenol A, and (ii) at least one aromatic compound having at least one vinyl substituent, preferably styrene. The standard way of obtaining the BPA is by crystallization of the BPA/phenol adduct or by precipitation in toluene. Other options are distillation or extraction of the BPA from the pyrolysis product mixture. Other products such as styrene or phenol can be separated by distillation.

The process according to the invention can be carried out with the aid of a suitably configured pyrolysis device. The invention thus further provides a pyrolysis device for producing pyrolysate from pyrolysis feedstock, comprising at least one metering device for feeding in pyrolysis feedstock, at least one heatable reactor for the pyrolysis, and at least one pyrolysate collector, characterized in that said heatable reactor for the pyrolysis includes at least one heating unit that can be used for temperature control of the reactor at a temperature of 300° C. to 700° C. and also at least one inlet for pyrolysis feedstock and at least one separate outlet for pyrolysate; and that the metering device and heatable reactor for the pyrolysis are arranged and configured in relation to one another such that the metering device is connected via at least one supply line to an inlet for the pyrolysis feedstock of said reactor; and that the heatable reactor for the pyrolysis and the pyrolysate collector are in fluid communication with one another such that it is possible for the preferably gaseous pyrolysate to be discharged from said pyrolysate outlet and for the discharged pyrolysate to be introduced into the pyrolysate collector; and that at least one pyrolysate collector includes at least one cooling device, temperature-controlled at a temperature below 300° C., that in said collector can be used to lower the temperature of the pyrolysate discharged from said reactor to less than 300° C., with the formation of a pyrolysis product selected from pyrolysate condensate, pyrolysate resublimate or a mixture thereof, and including at least one container for collecting and discharging the pyrolysis product obtained by cooling; and at least one metering device for feeding in pyrolysis feedstock, at least one heatable reactor for the pyrolysis, and at least one pyrolysate collector are arranged and configured in relation to one another such that they can be operated concomitantly.

The heating unit used for the heatable reactor may for example be a heating element, for example a heating coil or heating plates, or a device for heating a gas stream and for introducing the heated gas stream into the reactor.

In a preferred embodiment, the reactor additionally includes at least one connection to a gas source with which a gas stream in the reactor, preferably having a flow rate, as a superficial flow rate, of between 0.01 m/s and 20 m/s, flows via a regulator, for example a valve, through the reactor into the pyrolysate collector. If a fixed-bed reactor is chosen as the reactor, it is preferable according to the invention when the flow rate of the gas stream in the reactor, as the superficial velocity, is in the range from 0.03 m/s to 1 m/s. If a fluidized-bed reactor is chosen as the reactor, it is preferable according to the invention the flow rate of the gas stream in the reactor, as the superficial velocity, is in the range from 0.5 m/s to 2 m/s. If an entrained-flow reactor is chosen as the reactor, it is preferable according to the invention the flow rate of the gas stream in the reactor, as the superficial velocity, is in the range from 5 m/s to 20 m/s.

The gas stream from the gas source can for example be heated by the heating unit before it is introduced into the reactor as described above.

The pyrolysate collector of the device according to the invention preferably comprises a cooling device that in said collector can be used to lower the temperature of the pyrolysate discharged from said reactor to less than 50° C. (more preferably to less than 30° C.), with the formation of a pyrolysis product. Cooling units that work according to the heat exchanger principle are particularly suitable for this.

A "fluid connection" is in accordance with the invention understood as meaning a part of the device that connects parts of the system to one another and through which a substance that may be in any state of matter can be transported from one plant component to the next, for example a supply line in the form of a pipe.

The invention further provides for the use of a pyrolysis device of the abovementioned subject matter of the invention for the recovery of organic compound having at least two hydroxyl groups employed in the production of polycarbonate-containing compounds with concomitant recovery of styrene used in the production of polystyrene-containing compound, through concomitant pyrolysis of said polycarbonate-containing compound and said polystyrene-containing compound.

In a preferred embodiment of the use, the pyrolysis device is in addition to said concomitant styrene recovery used for the recovery of bisphenol A employed in the production of poly carbonate-containing compound.

The process according to the invention and the device according to the invention contribute to achieving the object set out above and in step (c) of the process provide as the pyrolysis product a composition comprising at least, in each case based on the total weight of the composition, (i) between 25% and 80% by weight of a total amount of at least one aromatic compound having at least two hydroxyl groups, preferably according to the general formula (I) above, very particularly preferably bisphenol A, (ii) more than 1% by weight of a total amount of at least one aromatic compound having exactly one hydroxyl group, preferably phenol, (iii) more than 1.5% by weight of a total amount of at least one aromatic compound having at least one vinyl substituent, preferably styrene or α-methylstyrene, where the proportions by weight of components (i) to (iii) together with the proportions by weight of other ingredients of the composition add up to 100% by weight.

It is preferable when the composition includes a small amount of high-boiling constituents. A preferred embodiment of the above composition therefore contains between 0.5% and 10.0% by weight of a total amount of at least one organic compound without a hydroxyl group having a boiling point at 1013 mbar of at least 300° C.

In a likewise preferred embodiment, the composition contains between 25% and 80% by weight of a total amount of aromatic compounds having at least two hydroxyl groups selected from 4,4'-dihydroxybiphenyl, bisphenol A, 2,4-bis(4-hydroxyphenyl)-2-methylbutane, 1,1-bis(4-hydroxyphenyl)cyclohexane, 1,1-bis(4-hydroxyphenyl)-3,3,5-trimethylcyclohexane, 4,4'-dihydroxydiphenyl sulfide, 4,4'-dihydroxydiphenyl sulfone, and also the di- and tetrabrominated or chlorinated derivatives thereof, for example 2,2-bis(3-chloro-4-hydroxyphenyl)propane, 2,2-bis(3,5-dichloro-4-hydroxyphenyl)propane or 2,2-bis(3,5-dibromo-4-hydroxyphenyl)propane, or mixtures thereof.

It is further additionally preferred when the abovementioned features of the abovementioned embodiments of components (i) and (ii) of the composition are combined.

In summary but without limitation, the following aspects 1 to 35 of the invention are to be regarded as further embodiments:

1. A pyrolysis process, comprising at least the following steps:
   (a) introducing of a pyrolysis feedstock that includes at least material comprising a mixture of polycarbonate-containing compound and polystyrene-containing compound into a reactor;
   (b) degradation of at least the material of the pyrolysis feedstock introduced in step (a) in the reactor at a temperature of 300° C. to 700° C. to obtain a gas-phase product as pyrolysate and a non-gas-phase pyrolysis residue, wherein
      (i) during said breakdown, the amount of oxygen gas in the reactor is not more than 2.0% by volume based on the total volume of the gases present in the reactor, and
      (ii) during said breakdown, the pyrolysate is discharged from the reactor, and
      (iii) said pyrolysis residue is discharged from the reactor;
   (c) cooling of the discharged pyrolysate to a temperature of less than 300° C. to obtain pyrolysis product selected from pyrolysate condensate, pyrolysate sublimate or a mixture thereof,
   (d) optionally working up of the pyrolysis product.
2. The process according to aspect 1, characterized in that the reactor is selected from a continuous stirred-tank reactor (CSTR), fixed-bed reactor, fluid-bed reactor, screw reactor, screw-conveyor reactor, entrained-flow reactor, entrainment-flow reactor, rotary-tube reactor, fluid-bed reactor, and drum reactor, in particular selected from continuous stirred-tank reactor (CSTR), fixed-bed reactor (especially with continuous bed exchange (shaft reactor) with internal heat exchangers), a screw reactor, a screw-conveyor reactor, an entrained-flow reactor, rotary-tube reactor or fluidized-bed reactor.
3. The process according to either of aspects 1 or 2, characterized in that the temperature in step (b) is from 350° C. to 650° C., preferably between 400° C. and 650° C., particularly preferably from 420° C. to 600° C., very particularly preferably from 450° C. to 580° C.
4. The process according to any of the preceding aspects, characterized in that the introduced pyrolysis feedstock is temperature-controlled at 300° C. to 700° C. and that, on reaching this target temperature, the introduced pyrolysis feedstock is temperature-controlled the residence time of the correspondingly temperature-controlled pyrolysis feedstock until the time of discharge of the pyrolysis residue resulting therefrom is from 1 second to 2 hours, preferably between 2 minutes and 60 minutes.
5. The process according to any of the preceding aspects, characterized in that the discharge of the pyrolysate from the reactor is ensured by a gas stream passed through the reactor or by suction, and preferably by the residence time of the pyrolysate, as the period between the time of introduction of said material introduced into the reactor in step (a) and the time of discharge of the resulting pyrolysate, being from 0.1 seconds to 10 seconds, preferably between 0.5 seconds and 5 seconds, more preferably 0.5 seconds to 2 seconds.
6. The process according to any of the preceding aspects, characterized in that the discharge of the pyrolysate from the reactor is ensured by a gas stream passed through the reactor, the flow rate of which in the reactor, as the superficial velocity, being in the range from 0.01 m/s to 20 m/s.
7. The process according to any of the preceding aspects, characterized in that the pyrolysate in the reactor is in the gas phase.
8. The process according to any of the preceding aspects, characterized in that the pyrolysis residue in the reactor is solid.
9. The process according to any of the preceding aspects, characterized in that at least steps (a) and (b) run concomitantly in the context of continuous process control.
10. The process according to any of the preceding aspects, characterized in that the amount of oxygen gas in the reactor in step (b) is not more than 0.5% by volume, preferably 0.1% by volume, in each case based on the total volume of the gases present in the reactor.
11. The process according to any of the preceding aspects, characterized in that the reactor packed with said material is filled with inert gas, in particular with nitrogen, argon, CO2, NO or mixtures thereof.
12. The process according to aspect 11, characterized in that the inert gas may additionally be admixed with reactive gases other than oxygen gas, in particular gases selected from methane, gaseous $H_2O$, hydrogen gas or mixtures thereof.
13. The process according to any of the preceding aspects, characterized in that the polycarbonate-containing compound is at least one compound that contains at least ten

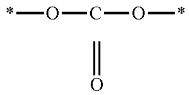

structural units, where * denotes a valence of the polymer backbone
14. The process according to any of the preceding aspects, characterized in that the polystyrene-containing compound is at least one polymer that contains at least ten repeat units of the formula $$*\!-\!CR^1Ph-CH_2-\!*$$

where * denotes a valence of the repeat unit of the polymer backbone, $R^1$ is a hydrogen atom or a methyl group, and Ph is a phenyl group optionally substituted with at least one group selected from $C_1$ to $C_4$ alkyl group and halogen atom (especially chlorine).
15. The process according to any of the preceding aspects, characterized in that the polycarbonate-containing compound is at least one compound obtained by reacting (i) at least one aromatic compound having at least two hydroxyl groups, preferably bisphenol A, and (ii) phosgene or diphenyl carbonate.
16. The process according to any of the preceding aspects, characterized in that the pyrolysis feedstock, more particularly the material, includes a limited total amount of phosphorus-containing organic compound such that, based on the total weight of the pyrolysis feedstock, the proportion introduced into the pyrolysis feedstock by this total amount of phosphorus-containing organic compound is from 0% by weight to not more than 0.5% by weight of phosphorus, preferably from 0% by weight to not more than 0.1% by weight of phosphorus, more preferably from 0% by weight to not more than 0.05% by weight of phosphorus, and particularly preferably from 0% by weight to not more than 0.01% by weight of phosphorus.

17. The process according to aspect 16, characterized in that the phosphorus present in said phosphorus-containing organic compound has a formal oxidation state of +5.

18. The process according to either of aspects 16 and 17, characterized in that said phosphorus-containing organic compound is selected from at least one compound of the group consisting of organic phosphoric esters, organic phosphonic esters, organic phosphazenes, and phosphonate amines, especially organic phosphoric esters and organic phosphonic esters.

19. The process according to any of aspects 16 to 18, characterized in that the phosphorus-containing organic compound is selected from at least one compound of the general formula (IV)

(IV)

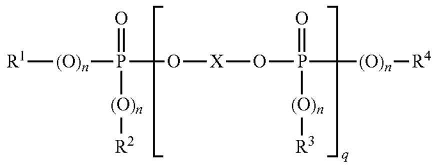

where $R^1$, $R^2$, $R^3$, and $R^4$ are each independently optionally halogenated C1 to C8 alkyl, C5 to C6 cycloalkyl optionally substituted by alkyl, preferably C1 to C4 alkyl, and/or halogen, preferably chlorine or bromine, C6 to C20 cycloalkyl optionally substituted by alkyl, preferably C1 to C4 alkyl, and/or halogen, preferably chlorine or bromine, or C7 to C12 aralkyl optionally substituted by alkyl, preferably C1 to C4 alkyl, and/or halogen, preferably chlorine or bromine, n is each independently 0 or 1, preferably 1, q is a number from 0 to 30, and X is a single- or multiring aromatic radical having 6 to 30 carbon atoms, or a linear or branched aliphatic radical having 2 to 30 carbon atoms, which may be OH-substituted and may contain up to 8 ether bonds.

20. The process according to any of aspects 16 to 19, characterized in that the pyrolysis feedstock in step (a) comprises at least one polycarbonate-containing compound and a limited total amount of phosphorus-containing organic compound such that, based on the total weight of the pyrolysis feedstock, the proportion introduced by this total amount of phosphorus-containing organic compound is from 0% by weight to not more than 0.5% by weight of phosphorus, preferably from 0% by weight to not more than 0.10% by weight of phosphorus, more preferably from 0% by weight to not more than 0.05% by weight of phosphorus, and particularly preferably from 0% by weight to not more than 0.01% by weight of phosphorus and optionally at least one polystyrene-containing compound.

21. The process according to any of the preceding aspects, characterized in that said material is introduced into the reactor in the form of solid particles, especially in the form of a granular mixture.

22. The process according to aspect 21, characterized in that the solid particles, more particularly the loose, solid particles of the granular mixture of said material introduced into the reactor, have an average diameter $X_{50.3}$ (volume average) of from 0.01 mm to 5 cm.

23. The process according to any of the preceding aspects, characterized in that said pyrolysis feedstock in step (a) also comprises in addition to said material at least one filler.

24. The process according to aspect 23, characterized in that the filler is at least one metal oxide not catalytically active in the pyrolysis of polycarbonate that preferably selected from $SiO_2$.

25. The process according to any of the preceding aspects, characterized in that said pyrolysis feedstock in step (a) also comprises in addition to said material at least one catalyst influencing the breakdown reaction of said material.

26. The process according to aspect 25, characterized in that said catalyst is at least one compound from the group consisting of inorganic salts, minerals, metal oxides, mixed oxides, clays, and zeolites.

27. The process according to either of aspects 25 and 26, characterized in that the catalyst is a basic catalyst.

28. The process according to any of aspects 25 to 27, characterized in that the catalyst is a heterogeneous catalyst.

29. The process according to any of aspects 1 to 28, characterized in that said pyrolysis feedstock contains said material in a total amount based on the total weight thereof of 10.0% to 80.0% by weight, more preferably 30.0% to 70.0% by weight.

30. A pyrolysis device for producing pyrolysate from pyrolysis feedstock, comprising at least one metering device for feeding in pyrolysis feedstock, at least one heatable reactor for the pyrolysis, and at least one pyrolysate collector, characterized in that said heatable reactor for the pyrolysis includes at least one heating element that can be used for temperature control of the reactor at a temperature of 300° C. to 700° C. and also at least one inlet for pyrolysis feedstock and at least one separate outlet for pyrolysate; and that the metering device and heatable reactor for the pyrolysis are arranged and configured in relation to one another such that the metering device is connected via at least one supply line to an inlet for the pyrolysis feedstock of said reactor; and that the heatable reactor for the pyrolysis and the pyrolysate collector are in fluid communication with one another such that it is possible for the preferably gaseous pyrolysate to be discharged from said pyrolysate outlet and for the discharged pyrolysate to be introduced into the pyrolysate collector; and that at least one pyrolysate collector includes at least one cooling device, temperature-controlled at a temperature below 300° C., that in said collector can be used to lower the temperature of the pyrolysate discharged from said reactor to less than 300° C., with the formation of a pyrolysis product selected from pyrolysate condensate, pyrolysate sublimate or a mixture thereof, and including at least one container for collecting and discharging the pyrolysis product obtained by cooling; and at least one metering device for feeding in pyrolysis feedstock, at least one heatable reactor for the pyrolysis, and at least one pyrolysate collector are arranged and configured in relation to one another such that they can be operated concomitantly.

31. The use of a pyrolysis device according to aspect 30 for the recovery of organic compound having at least two hydroxyl groups employable in the production of polycarbonate-containing compounds with concomitant recovery of styrene used in the production of polystyrene-containing compound, through concomitant pyrolysis of said polycarbonate-containing compound and said polystyrene-containing compound.

32. The use according to aspect 31, characterized in that the pyrolysis device is used for the recovery of bisphenol A employed in the production of polycarbonate-containing compound.

33. A composition comprising at least, in each case based on the total weight of the composition, (i) between 25% and 80% by weight of a total amount of at least one aromatic compound having at least two hydroxyl groups, preferably bisphenol A, (ii) more than 1% by weight of a total amount of at least one aromatic compound having exactly one hydroxyl group, preferably phenol, (iii) more than 1.5% by weight of a total amount of at least one aromatic compound having at least one vinyl substituent, preferably styrene or α-methylstyrene, where the proportions by weight within the parts by weight ranges from (i) to (iii) are selected such that the sum total of the selected proportions by weight from (i) to (iii) together with the parts by weight of other ingredients of the composition add up to 100% by weight.

34. The composition according to aspect 33, characterized in that the composition is a pyrolysis product.

35. The composition according to aspect 34, characterized in that the composition is a pyrolysis product obtained in a process according to any of aspects 1 to 29.

EXAMPLES

Example 1 (Inventive)

The pyrolysis of polycarbonate/ABS blend Bayblend® FC 85 from Covestro Deutschland AG (Leverkusen, Germany) (hereinafter referred to as PC blend) (free of phosphorus-containing organic compounds) was carried out at 500° C. in a fixed-bed reactor with a through-flow of $N_2$. The polycarbonate was introduced into the reactor in five $Al_2O_3$ crucibles with holder, each containing 2 g. The residence time of the polycarbonate blend was 30 min. The flow rate of the gas stream (superficial velocity) in the reactor was 0.07 m/s. Situated downstream of the reactor were two condensers for the separation and collection of the liquid components of the resulting pyrolysis product. The resulting content of carbonized material in the pyrolysis residue was determined by weighing the crucible after the pyrolysis. The gas downstream of the two condensers was characterized by GC. The components of the pyrolysis product obtained in the form of an oil were determined by GC-FID. This was done using an Agilent 7890A with a Supelco SPB 50 column. The pyrolysis oil was for this purpose diluted 1:50 or 1:100 with acetone.

Example 2 (Noninventive)

The pyrolysis of polycarbonate/ABS blend Bayblend® FC 85 from Covestro Deutschland AG was carried out at 800° C. in a fixed-bed reactor with a through-flow of $N_2$. The PC was introduced into the reactor in five $Al_2O_3$ crucibles with holder, each containing 2 g. The residence time of the PC blend was 30 min. The flow rate of the gas stream (superficial velocity) in the reactor was 0.07 m/s. Situated downstream of the reactor were two condensers for the separation and collection of the liquid components of the resulting pyrolysis product. The resulting content of carbonized material in the pyrolysis residue was determined by weighing the crucible after the pyrolysis. The gas downstream of the two condensers was characterized by GC. The components of the pyrolysis product obtained in the form of an oil were determined by GC-FID according to the analytical method described in example 1.

Result as proportions based on parts by weight of PC blend used:

| Pyrolysis temperature | Gas | Carbonized material | Other constituents* | Toluene* | Ethyl-benzene* | Styrene* | Phenol* | 4-tert-Butyl-phenol* | Phthalic acid* | BPA* |
|---|---|---|---|---|---|---|---|---|---|---|
| 500° C. (Ex. 1) | 7.5 | 10.8 | 23.3 | 0.3 | 0.5 | 7.8 | 11.9 | 0.2 | 0.3 | 34.5 |
| 800° C. (Ex. 2, comparative) | 9.4 | 7.9 | 19.8 | 0.5 | 0.8 | 11.5 | 20.7 | 0.3 | 0.1 | 18.2 |

*denotes constituents of the pyrolysis product

The invention claimed is:

1. A pyrolysis process, comprising at least the following steps:

(a) introducing of a pyrolysis feedstock that includes at least:

(i) material comprising a mixture of polycarbonate-containing compound and polystyrene-containing compound into a reactor; and (ii) one catalyst from the group consisting of aluminum oxide, magnesium oxide, zirconium oxide, titanium oxide, chromium oxide, zinc oxide, tin oxide, combinations of aluminum oxide with magnesium oxide and/or calcium oxide, aluminosilicates, silicon aluminum phosphates, silicalite, spinels, and clays;

(b) degrading of at least the material of the pyrolysis feedstock introduced in step (a) in the reactor at a temperature of 300° C. to 700° C. to obtain a gas-phase product as pyrolysate and a non-gas-phase pyrolysis residue, wherein (i) during breakdown, the amount of oxygen gas in the reactor is not more than 2.0% by volume based on the total volume of the gases present in the reactor;

(ii) during said breakdown, the pyrolysate is discharged from the reactor; and (iii) said pyrolysis residue is discharged from the reactor; and (c) cooling of the discharged pyrolysate to a temperature of less than 300° C. to obtain pyrolysis product selected from pyrolysate condensate, pyrolysate resublimate or a mixture thereof, wherein the pyrolysis product comprises aromatic compounds having at least one hydroxyl group.

2. The process as claimed in claim 1, wherein the temperature in step (b) is from 350° C. to 650° C.

3. The process as claimed in claim 1, wherein the introduced pyrolysis feedstock is temperature-controlled at 300° C. to 700° C. and that a residence time of the temperature-controlled pyrolysis feedstock is from 1 second to 2 hours.

4. The process as claimed in claim 1, wherein the discharge of the pyrolysate from the reactor is ensured by a gas stream passed through the reactor or by suction.

5. The process as claimed in claim 1, wherein the discharge of the pyrolysate from the reactor is ensured by a gas stream passed through the reactor, the flow rate of which in the reactor, as the superficial velocity, being in the range from 0.01 m/s to 20 m/s.

6. The process as claimed in claim 1, wherein at least steps (a) and (b) run concomitantly in the context of continuous process control.

7. The process as claimed in claim 1, wherein the amount of oxygen gas in the reactor in step (b) is not more than 0.5% by volume based on the total volume of the gases present in the reactor.

8. The process as claimed in claim 1, wherein the reactor packed with said material is filled with inert gas.

9. The process as claimed in claim 1, wherein the polycarbonate-containing compound is at least one compound that contains at least ten

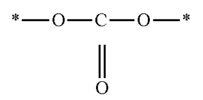

structural units, where * denotes a valence of the polymer backbone.

10. The process as claimed in claim 1, wherein the polystyrene-containing compound is at least one polymer that contains at least ten repeat units of the formula

*—CR1Ph—CH2—* where * denotes a valence of the repeat unit of the polymer backbone, R1 is a hydrogen atom or a methyl group, and Ph is a phenyl group.

11. The process as claimed in claim 1, wherein the polycarbonate-containing compound is at least one compound obtained by reacting (i) at least one aromatic compound having at least two hydroxyl groups and (ii) phosgene or diphenyl carbonate.

12. The process as claimed in claim 1, wherein the pyrolysis feedstock includes a defined total amount of phosphorus-containing organic compound such that, based on the total weight of the pyrolysis feedstock, the proportion introduced into the pyrolysis feedstock by this total amount of phosphorus-containing organic compound is from 0% by weight to not more than 0.5% by weight of phosphorus.

13. The process as claimed in claim 12, wherein the phosphorus present in said phosphorus-containing organic compound has a formal oxidation state of +5.

14. The process as claimed in claim 12, wherein said phosphorus-containing organic compound is selected from at least one compound of the group consisting of organic phosphoric esters, organic phosphonic esters, organic phosphazenes, and phosphonate amines.

15. The process as claimed in claim 12, wherein the phosphorus-containing organic compound is selected from at least one compound of the general formula (IV)

(IV)

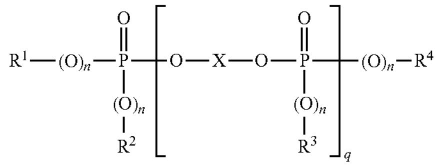

where

R1, R2, R3, and R4 are each independently optionally halogenated $C_1$ to $C_8$ alkyl, $C_5$ to $C_6$ cycloalkyl optionally substituted by alkyl and/or halogen, C6 to C20 cycloalkyl optionally substituted by alkyl and/or halogen, or C7 to C12 aralkyl optionally substituted by alkyl- and/or halogen, n is each independently 0 or 1;

q is a number from 0 to 30; and

X is a single- or multiring aromatic radical having 6 to 30 carbon atoms, or a linear or branched aliphatic radical having 2 to 30 carbon atoms, which may be OH-substituted and may contain up to 8 ether bonds.

16. The process as claimed in claim 1, wherein said material is introduced into the reactor in the form of solid particles.

17. The process as claimed in claim 1, wherein said pyrolysis feedstock in step (a) also comprises in addition to said material at least one filler.

18. The process as claimed in claim 1, wherein said pyrolysis feedstock contains said material in a total amount based on the total weight thereof of 10.0% to 80.0% by weight.

19. The process as claimed in claim 1, wherein the catalyst is a heterogeneous catalyst comprising solid particles having an average diameter in a range of 0.01 mm to 5 cm.

* * * * *